(12) United States Patent
Escaich et al.

(10) Patent No.: US 7,763,594 B2
(45) Date of Patent: Jul. 27, 2010

(54) COMPOSITIONS FOR THE TREATMENT OF OSTEOARTHRITIS AND TO NOURISH THE SYNOVIAL FLUID

(75) Inventors: Josep F. Escaich, Barcelona (ES); Joaquima S. Guix, Sant Genis de Palafolls (ES); Ana R. Ubia, Barcelona (ES); Ramon R. Ruhi, Barcelona (ES); Juan V. Recio, Palafolls (ES); Ana Maria G. Torrent, Blanes (ES)

(73) Assignee: Bioiberica, S.A., Barcelona (ES)

( * ) Notice: Subject to any disclaimer, the term of this patent is extended or adjusted under 35 U.S.C. 154(b) by 680 days.

(21) Appl. No.: 11/605,453

(22) Filed: Nov. 29, 2006

(65) Prior Publication Data
US 2007/0196438 A1 Aug. 23, 2007

Related U.S. Application Data

(60) Provisional application No. 60/740,670, filed on Nov. 30, 2005.

(51) Int. Cl.
*A61K 31/728* (2006.01)
*A61K 31/737* (2006.01)
*A61K 31/7105* (2006.01)
*A61K 51/08* (2006.01)

(52) U.S. Cl. .............................. 514/54; 514/12; 514/44

(58) Field of Classification Search .................. 514/12, 514/44, 54
See application file for complete search history.

(56) References Cited

U.S. PATENT DOCUMENTS

| 6,476,005 B1 * | 11/2002 | Petito et al. ..................... 514/62 |
| 6,511,958 B1 * | 1/2003 | Atkinson et al. ................ 514/2 |
| 6,607,745 B2 * | 8/2003 | Leneau ........................ 424/439 |
| 2002/0068718 A1 | 6/2002 | Pierce |
| 2005/0084518 A1 * | 4/2005 | Arai ............................ 424/439 |

OTHER PUBLICATIONS

Bourgeois et al, Osteoarthritis and Cartilage, 1998, 6 (Supplement A), 25-30.*
Database Biosis, Biosciences Information Service, Philadephia, PA, Apr. 2007, Torrent et al., "Evaluation of the potential efficacy of a natural rooster comb extract (Hyal-Joint (R)) in maintaining joint integrity and function".

* cited by examiner

*Primary Examiner*—Shaojia Anna Jiang
*Assistant Examiner*—Ganapathy Krishnan
(74) *Attorney, Agent, or Firm*—Sughrue Mion, PLLC

(57) ABSTRACT

The present invention relates to the use of compositions comprising hyaluronic acid and dermatan sulphate for the preparation of medicaments to be orally administered for the treatment of osteoarthritis and osteoarthritis-associated articular pain. The present invention also relates to the use of compositions comprising hyaluronic acid and dermatan sulphate for the preparation of a food or a food supplement to nourish the synovial fluid in a joint, and to improve articular mobility. The compositions may also contain collagen hydrolysate and nucleic acids.

16 Claims, 4 Drawing Sheets

COMPOSITIONS FOR THE TREATMENT OF OSTEOARTHRITIS AND TO NOURISH THE SYNOVIAL FLUID

CROSS REFERENCE TO RELATED APPLICATIONS

This application claims priority from U.S. Provisional Application No. 60/740,670 filed on Nov. 30, 2005 in the United States Patent and Trademark Office, the entire disclosure of which is incorporated herein by reference.

BACKGROUND OF THE INVENTION

1. Technical Field

The present invention relates to the use of compositions to be orally administered for the treatment of osteoarthritis and pain associated to it. Additionally, the present invention relates to the use of compositions in the preparation of food or food supplements for nourishing the synovial fluid.

2. Related Art

Osteoarthritis is a degenerative joint disease which affects most people from the age of 65.

Osteoarthritis can be defined as the degeneration of the hyaline articular cartilage. Secondarily, the synovial membrane and the subchondral bone (bone in contact with the cartilage) are affected, and new bone is formed on the margins of joint surfaces.

The cartilage allows bones to move, by sliding over one another. It also absorbs tensions generated by physical movement. In osteoarthritis, the cartilage surface breaks and wears out, causing bones to move against each other, causing friction, pain, swelling and loss of articular mobility. With time, the joint may deform.

Under normal conditions, cartilage renewal is a very slow process, which consists of a constant synthesis (anabolism) and degradation (catabolism) of components of the extracellular matrix. The chondrocyte is the cell responsible for this metabolism, which must be perfectly coordinated.

Although the ethiology of osteoarthritis is still unknown, it is nowadays generally accepted that the first alterations occur at the chondrocyte level, eventually leading to a joint affected by osteoarthritis.

Several risk factors for osteoarthritis have been described, namely, age, inheritance, obesity, excess weight related disorders, sport-related physical stress, injuries or traumatisms, work activity and bone mineral density.

There is no definitive treatment for osteoarthritis. We highlight the following current options for therapy:

Symptomatic-action drugs which have a rapid action. Among these are: analgesics, nonsteroidal anti-inflammatory drugs (NSAIDs), corticoids and cyclooxygenase 2 (COX-2) selective inhibitors. The use of some of these drugs involves a high risk of potentially severe side effects, such as gastrointestinal problems derived from the use of NSAIDs.

Symptomatic-action drugs which act in a slower manner. These are better known as SYSADOA (Symptomatic Slow-Acting Drug for Osteoarthritis) (M. G. Lequesne, *Rev. Rhum.* (Eng./Ed.) 61;69-73 (1994); B. F. Leeb et al., *J. Rheumatol.* 27:205-211 (2000)). These substances include hyaluronic acid, chondroitin sulphate, glucosamine hydrochloride and the so-called glucosamine sulphate. This group of drugs is characterized by general efficacy similar to that of NSAIDs and also by greater safety and a more prolonged action, even a few months after treatment suspension (carry-over or residual effects). A number of clinical assays with hyaluronic acid (M. Dougados *Semin. Artritis. Rheum.* 30(2 Suppl. 1):19-25 (2000)) and with chondroitin sulphate (D. Uebelfart et al., *Osteoarthritis Cart.* 12:269-276 (2004)) have shown that both compounds, as well as acting as SYSADOA, may have an influence on the course of osteoarthritis, either by slowing its progress or by delaying its onset, by acting as S/DMOAD drugs (Structure/Disease Modifying anti-Osteoarthritis Drug).

Hyaluronic acid is a naturally occurring non-sulphated glycosaminoglycan with a polymeric structure of disaccharides of N-acetyl-D-glucosamine and D-glucuronic acid. It is extracted mainly from organs or tissues of birds and mammals. It is one of the primary components of cartilages, synovial membranes and synovial fluid. The endogenous hyaluronic acid is primarily synthesised by synoviocytes, in addition to, although to a lesser extent, by chondrocytes. In osteoarthritis patients, the synovial fluid shows a lower concentration of endogenous hyaluronic acid; therefore, the lubricant effect and the viscoelastic properties of the synovial fluid are reduced, since the synovial fluid, being a viscous fluid present in the joint cavity, lubricates and nourishes the joint cartilage, thus reducing the friction between the joint surfaces, and facilitating movement of the joint. The preferred route for administration of hyaluronic acid in the treatment of osteoarthritis is intra-articular. The action of intra-articular hyaluronic acid lies in the improvement of the mobility of joints having a degenerate cartilage surface and synovial fluid alterations.

Hyaluronic acid is also used in the field of intra-articular implants, in ophthalmology, for accelerating the healing of wounds, and in cosmetics.

Dermatan sulphate, otherwise known as chondroitin sulphate B, is a naturally occurring glycosaminoglycan with a polymer structure primarily comprising disaccharides of sulphated N-acetyl-D-galactosamine and L-iduronic acid. Several disaccharide units contain N-acetyl-D-galactosamine lacking sulphate groups, or substitutions of L-iduronic acid for D-glucuronic acid. It is obtained from organs or tissue of birds and mammals.

Dermatan sulphate is used, mixed with other glycosaminoglycans, for the treatment of thromboses by the subcutaneous route, and in the manufacturing of cosmetics.

Collagen hydrolysate comprises a mixture of aminoacids and low molecular weight peptides. It is obtained through the controlled enzymatic hydrolysis of collagenous protein in skin and other conjunctive tissues. It is primarily used in cosmetics.

U.S. Patent Application Publication No. 2005/0084518 describes a health food containing hyaluronic acid and dermatan sulphate. This food differs from the compositions in this invention in that it is useful for skin embellishment.

In U.S. Patent Application Publication No. 2002/0068718 the use of orally administered hyaluronic acid in the treatment for osteoarthritis is described. Chondroprotective compositions containing hyaluronic acid are also described. In addition to hyaluronic acid, the compositions may contain glucosamine sulphate and/or chondroitin sulphate.

U.S. Pat. No. 6,607,745 describes a food supplement essentially consisting of hyaluronic acid for ameliorating articular pain and other malaise associated to osteoarthritis.

The problem to be solved by the present invention is to provide a composition more efficacious than hyaluronic acid for treating osteoarthritis and osteoarthritis-associated pain, for nourishing the joint and for improving articular mobility.

To date, no description can be found of the use of a composition comprising hyaluronic acid and dermatan sulphate in the treatment, prevention or prophylaxis of osteoarthritis or osteoarthritis-associated articular pain.

Furthermore, to date no description can be found of the use of a composition comprising hyaluronic acid and dermatan sulphate in the manufacturing of a food or food supplement for the nourishment of a joint, particularly for the nourishment of the synovial fluid present in the joint, o for improving the articular mobility.

SUMMARY OF THE INVENTION

The present invention relates to the use of compositions comprising hyaluronic acid and dermatan sulphate for the preparation of medicaments to be orally administered for the treatment, prevention or prophylaxis of osteoarthritis in mammals.

Another aspect of the present invention is the use of compositions which include hyaluronic acid and dermatan sulphate in the manufacturing of medicaments to be orally administered for the treatment, prevention or prophylaxis of osteoarthritis-associated articular pain.

In a preferred embodiment, dermatan sulphate is present in an amount efficacious for enhancing the anti-osteoarthritic action of hyaluronic acid.

In a more preferred embodiment, the weight ratio of hyaluronic acid to dermatan sulphate is comprised between 1:0.05 and 1:0.7. A particularly preferred weight ratio is between 1:0.1 and 1:0.5.

In an equally preferred embodiment, compositions also contain collagen hydrolysate. The preferred weight ratio of hyaluronic acid to dermatan sulphate to collagen hydrolysate is between 1:0.05:0.05 and 1:0.7:0.7. A particularly preferred weight ratio is between 1:0.1:0.1 and 1:0.5:0.5.

In an equally preferred embodiment, the compositions also contain collagen hydrolysate and nucleic acids.

Another aspect of the invention is the use of compositions comprising hyaluronic acid and dermatan sulphate for the preparation of foods or food supplements for nourishing a joint. Preferably, for nourishing the synovial fluid present in the joint.

Another aspect of the invention is the use of compositions comprising hyaluronic acid and dermatan sulphate for the preparation of foods or food supplements for improving articular mobility.

In a another preferred embodiment, the compositions contained more over collagen hydrolysate. The preferred weight ratio of hyaluronic acid, dermatan sulphate to collagen hydrolysate is comprised between 1:0.1:0.1 and 1:0.5;0.5.

In a preferred embodiment, the compositions also include collagen hydrolysate and nucleic acids.

The phrase "treatment of osteoarthritis" is also meant to refer to the symptomatic treatment of osteoarthritis (pain and functional disability).

All the uses claimed in the present invention are linked to each other forming one single inventive concept.

Hyaluronic acid and dermatan sulphate to be used in the present invention may be naturally occurring, i.e. derived from birds and mammals, semi-synthetic products or products obtained biotechnologically, which, when necessary, can be transformed by chemical methods.

The phrase "semi-synthetic product" refers to the product obtained performing structural changes through chemical reactions from the natural extract.

The naturally occurring hyaluronic acid can be obtained from bird or mammal tissues, for example from vitreous humour, mammal skin, umbilical chord, bird crest and by fermentation using a microorganism, such as Streptococcus, following the procedures described in the literature (D. A. Swann, *Biochim. Biophys. Acta* 156:17-30 (1968); H. Akasaka et al., Prepints of the XIVth I.F.S.C.C. Congress, Barcelona 1:265-281 (1986); U.S. Pat. No. 4,780,414).

Dermatan sulphate can be obtained from bird or mammal tissues, e.g. from pork o bovine mucose and bird crests, following procedures described in the literature (N. Volpi, *Anal. Biochem.* 218:382-391 (1994); R. Del Bono et al., U.S. Pat. No. 5,116,963).

Collagen hydrolysate can be obtained from the skin of mammals or cockscomb, following the procedures described in the literature ("Final Report on the Safety Assessment of Hydrolyzed Collagen", *Journal of the American College of Toxicology* 4, no. 5, 199-221, Mary Ann Liebert, Inc., Publishers, (1985)).

The collagen hydrolysate of the present invention has a proline content above 9%.

The average molecular weights for hyaluronic acid and dermatan sulphate used in the present invention may vary depending on the method of obtention. The average molecular weight for hyaluronic acid preferably is between 300,000 and 2,000,000 Dalton, more preferably between 500,000 and 1,000,000 Dalton; for dermatan sulphate, the average molecular weight is between 10,000 and 35,000 Dalton, more preferably between 15,000 and 25,000 Dalton.

The compositions of the present invention can be obtained directly from natural extracts derived from tissues of birds or mammals. Thus, for example, frozen cockscombs may be used, grinded and digested with a proteolytic enzyme. Subsequently, the enzyme is deactivated by heating and the solution is filtered. Next, the product is precipitated using solvents. After that, the product is filtered, washed with solvents and dried. Finally, the product may be milled. The product obtained contains hyaluronic acid, dermatan sulphate, collagen hydrolysate (in the form of low molecular weight aminoacids and peptides), and nucleic acids, or part of said components. The presence of all or part of said components, and their compositional ratio, is dependent on the procedure of obtention used (type of enzyme, temperature, reaction time and purification process).

If desired, the compositions of the present invention may be prepared by mixing the various components, which have been separately obtained, in the desired proportions. Thus, compositions can be prepared containing hyaluronic acid and dermatan sulphate; or hyaluronic acid, dermatan sulphate and collagen hydrolysate (low molecular weight aminoacids and peptides); or hyaluronic acid, dermatan sulphate, collagen hydrolysate and nucleic acids.

To be used in the treatment, prevention or prophylaxis of osteoarthritis, and for the treatment, prevention or prophylaxis of osteoarthritis-associated pain, the compositions of the invention are formulated in suitable pharmaceutical compositions (medicaments), using conventional techniques and excipients or vehicles, such as those described in *Remington: The Science and practice of Pharmacy*, edited by A. R. Gennaro, University of the Sciences in Philadelphia, 20$^{th}$ edition, USA.

The pharmaceutical compositions of the invention may be administered to the patient orally in the required doses. The pharmaceutical compositions of the invention include a therapeutically effective amount of the composition of the present invention depending said amount on several factors, such as the patient's physical condition, age, sex, particular composition and other well-known factors in the art. Also, it is understood that said dose of the active composition can be administered in single or multiple dose units in order to achieve the desired therapeutic effects.

The pharmaceutical compositions of the invention are generally in solid, liquid or gel form. Among the pharmaceutical compositions in solid form which can be prepared according to the present invention, powder, minigranules (pellets), tablets, dispersible granules, capsules, cachets and other galenic solid forms. The liquid forms include solutions, suspensions, emulsions and microspheres. Also contemplated are compositions in solid form which are desirably converted immediately prior to use into compositions in liquid form for oral administration. Said liquid forms include solutions, suspensions and emulsions.

For the manufacturing of food or food supplements (also known as functional foods or nutraceuticals) to be used according to the invention, the compositions of the invention are formulated together with suitable components and excipients used in nutrition. For example, food can be in solid or liquid form. Also contemplated are solid compositions which may be transformed prior to use into drink, soup or cream. Food supplements may be, for example, in the form of solid, liquid, emulsion, suspension or gel. In this case, also contemplated are compositions in solid form which can be transformed prior to use into liquid compositions or suspensions.

DETAILED DESCRIPTION OF THE EXEMPLARY EMBODIMENTS OF THE PRESENT INVENTION

Figure 1:
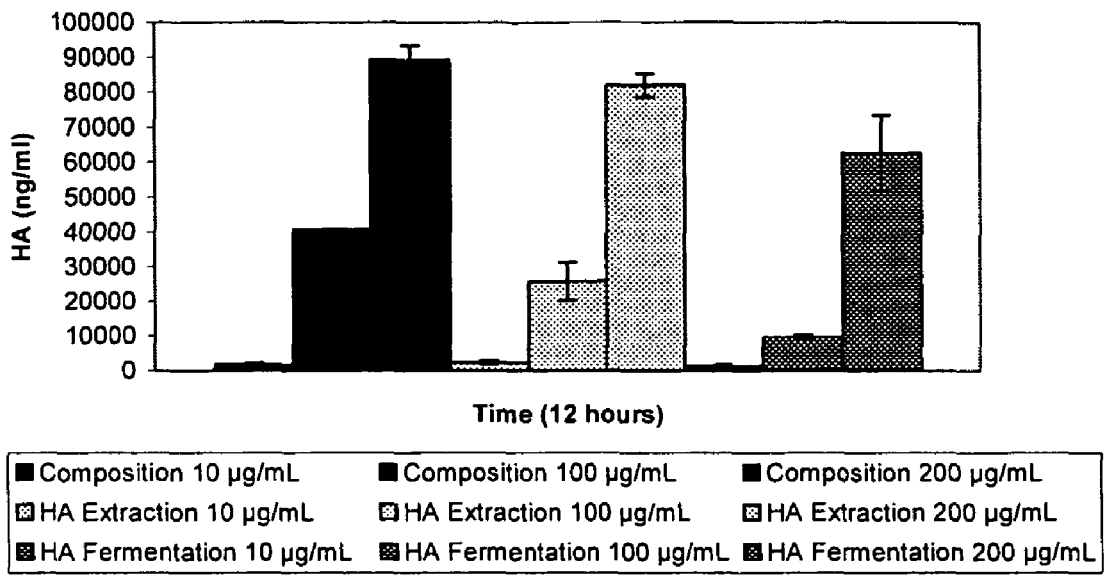
FIG. 1 shows the effect, after a 12-hour period, of a composition of the invention (55% hyaluronic acid, 15% dermatan sulphate, 15% collagen hydrolysate and 4% nucleic acids), of hyaluronic acid derived from bird tissue (HA extraction) and of hyaluronic acid derived from the microorganism fermentation (HA fermentation) on extracellular levels of endogenous hyaluronic acid synthesised by human osteoarthritic synoviocytes.

The following examples are merely illustrative and are not limitative of the scope of the present invention.

EXAMPLE 1

Determination of the Ability of a Composition of the Invention for Stimulating the Production of Endogenous Hyaluronic Acid by Human Synoviocytes. Comparative Study of Hyaluronic Acids and a Composition of the Invention The following procedure can be applied in the evaluation of the efficacy of any of the compositions of the present invention.

The aim was to study the effect of a composition of the invention and also of two hyaluronic acids on the synthesis of endogenous hyaluronic acid by synoviocytes, and to establish whether differences existed among them.

The composition used contained 55% hyaluronic acid, 15% dermatan sulphate, 15% collagen hydrolysate and 4% nucleic acids (weight ratio: 1:0.27:0.27:0.07).

One of the hyaluronic acids used was obtained from bird tissues (HA extraction) and had an average molecular weight of 1,000,000 Dalton (commercial product available from Bioibérica, S.A., www.bioiberica.com).

The other hyaluronic acid used was derived from microorganism fermentation (HA fermentation) and had an average molecular weight of 1,000,000 Dalton (commercial product available from IBC as sodium hyaluronate powder).

Materials and Methods

The composition of the invention, the HA extraction and the HA fermentation were separately incubated with synoviocytes for 12 and 24-hour periods. The following concentrations were used, both of the composition of the invention and of the hyaluronic acids: 10 µg/ml, 100 µg/ml and 200 µg/ml.

Synovial tissues were obtained from three osteoarthritic joints.

Synovial tissue was introduced into a sterile vial with DMEM (Dulbecco's Modification of Eagle's Medium) (2%), penicillin (150 U/ml), streptomycin (50 mg/ml) and amphotericin B (2 µg/ml), and then placed in a refrigerator (temperature: 0-4° C.) for transferral to the cell culture area. The synovial tissue was diced into fragments approximately sized to 2×2×2 mm$^3$. The fragments were washed three times in culture medium (RPMI 2% P/S/A). 20 ml of culture medium with 10% trypsin was added, and then incubated in a water bath at 37° C. for 10-15 minutes. Subsequently, the synovium was digested with 25 ml of collagenase solution [2 mg/ml type II collagenase; 5% fetal calf serum (FCS); 2% P/S/A; 1% L-glutamine; and deoxyribonuclease I 0.1 mg/ml or 150 U/l in RPMI]. The vial was introduced into a rotary shaker at 37° C. for approximately 2-4 hours. The cells were strained through a nylon filter with 25 µm diameter pores. A cell count was conducted and the cells were grown to a density of 5,000 to 10,000 cell/cm$^2$ in culture bottles of 25 or 75 cm$^2$ surface. The culture medium used was RPM supplemented with 10% FCS, 1% P/S and 1% L-glutamine. The synoviocytes used in the experiments were all from passages 2-3.

Following a 24-hour period culture, the synoviocytes (100,000 cells per well in a 24-well plate with 250 µl of medium) were stimulated using the composition of the invention, the HA extraction and the HA fermentation for 12 and 24-hour periods. Then, the supernatant of the different wells was harvested. The endogenous hyaluronic acid content was measured using an ELISA (Corgenix Inc. USA).

Results are shown as the average of 9 individual experiments performed on the cultures. Results are expressed as averages±S.D. and S.E. The statistical analysis was done using a two-tailed unpaired Student's T-test. A statistical difference is considered significant when p<0.05.

Results

Figure 2:
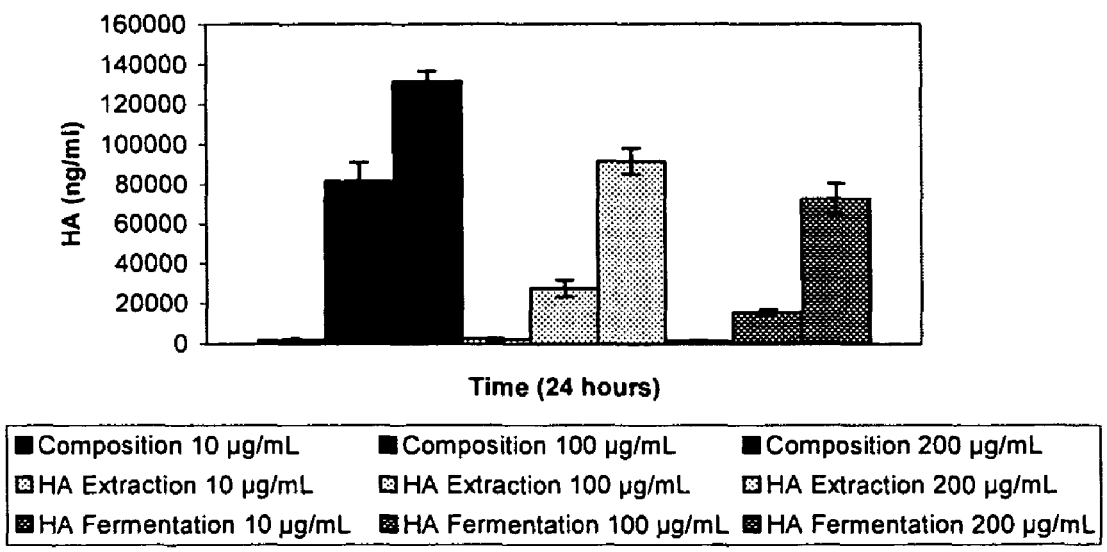
FIG. 2 shows the effect, after a 24-hour period, of a composition of the invention (55% hyaluronic acid, 15% dermatan sulphate, 15% collagen hydrolysate and 4% nucleic acids), of hyaluronic acid derived from bird tissues (HA extraction) and of hyaluronic acid derived from the microorganism fermentation (HA fermentation) on the extracellular levels of endogenous hyaluronic acid synthesised by human osteoarthritic synoviocytes.

Both the composition of the invention and the hyaluronic acids caused a dose dependent increase on the levels of endogenous hyaluronic acid measured in the supernatants of the synoviocyte cultures. Significant differences were found between the composition of the invention and the hyaluronic acids at the 100 and 200 µg/ml concentrations after the 12 and 24-hour periods (FIGS. 1 and 2).

After the 12-hour period and at the 200 µg/ml concentration, the highest measured levels were obtained in the cells grown in the composition of the invention (89,185 ng/ml), and the lowest levels were found in the cells grown in HA fermentation (62,618 ng/ml). This response pattern was also observed in the 100 µg/ml dose (composition of the invention=40,814 ng/ml; HA extraction=25,762 ng/ml; HA fermentation=9,724 ng/ml) (FIG. 1).

After the 24-hour period, the difference between the composition of the invention and the hyaluronic acids was more marked. At the 200 µg/ml concentration, the level measured in cells grown with the composition of the invention was 131,660 ng/ml, with the HA extraction the level was 91,538 ng/ml, and with the HA fermentation the level was 72,594 ng/ml. This response pattern was also observed at the 100 µg/ml dose (composition of the invention=81,550 ng/ml; HA extraction=27,634 ng/ml; HA fermentation=15,706 ng/ml) (FIG. 2).

Conclusions

With respect to the effect of the composition of the invention on measured levels of endogenous hyaluronic acid in the supernatants of cultured synoviocytes, its pattern was dose- and time-dependent.

After both the 12 and the 24-hour periods and at the 100 and 200 µg/ml doses, the composition of the invention stimulated the production of endogenous hyaluronic acid by human synoviocytes. Both doses showed a greater effect after the 24-hour incubation period.

As shown in both FIGS. 1 and 2 the assayed composition of the invention was significantly more efficacious than either of the two hyaluronic acids.

Because the composition of the invention assayed at a certain concentration contains 55% hyaluronic acid, and is more efficacious than the hyaluronic acid assayed at the same concentration, it can be stated that the rest of the components accompanying the hyalurinic acid in the composition of the invention, enhance the action of the hyaluronic acid.

Because the composition of the invention stimulates the production of endogenous hyaluronic acid by articular synoviocytes, and considering the relation between the decrease of endogenous hyaluronic acid content in the synovial fluid and the development of osteoarthritis, it can be stated that the composition of the invention is useful for the treatment of osteoarthritis, for nourishing the joints and for improving articular mobility.

EXAMPLE 2

Determination of Intestinal Absorption

Assays were performed on male OFA rats. The following parts of the small intestine were studied: duodenum, jejunum and ileum.

The duodenum is the first part of the small intestine and is situated between the stomach and the jejunum. After food is combined with gastric acid, it descends to the duodenum, where it mixes with the bile derived from the gall-bladder and with digestive liquids from the pancreas.

Jejunum is the part of the small intestine, measuring about 2.2 miters, extending from the duodenum to the ileum.

The ileum is the final part of the small intestine and it is located between the jejunum and the cecum, which is the first part of the large intestine.

The composition used contained 55% hyaluronic acid, 15% dermatan sulphate, 15% collagen hydrolysate and 4% nucleic acids (weight ratio: 1:0.27:0.27:0.07).

To evaluate the level of absorption, the everted rat intestinal sac technique was used.

To analyse the amount of absorbed composition, the technique described by Farndale et al. (*Connective Tissue Research* 9:247-248 (1982)) was followed for determining glycosaminoglycan content.

Results

The following absolute values were obtained for each part of the small intestine: 40% for the duodenum, 19% for the jejunum and 7% for the ileum.

Considered the results obtained, it can be stated that the composition is well absorbed in the small intestine, especially in the duodenum.

EXAMPLE 3

Inhibition of Metalloprotease Activity in Human Arthrosic Chondrocytes. Comparative Study of Two Compositions of the Invention, Hyaluronic Acid and Dermatan Sulphate The destruction of the cartilage matrix dependes mainly on the enzymatic degradation of its components. This structure dependes primarily on two types of existing molecules: collagen fibres and proteoglycanes. While degradation of collagen fibres leads to matrix instability and tissue swelling, degradation of the proteoglycans leads to softening of the cartilage and to loss of fixed charges. Both processes are characteristic of osteoarthritis. The enzymes responsible for degradation of the triple helix of collagen are called matrix metalloproteases (MMP). In patients with osteoarthritis, high levels of collagenases have been found, as well as a relationship between those levels and the severity of the osteoarthritic lesions.

The ethiology of osteoarthritis is still unknown. It is now recognized that early alterations occur in chondrocytes, due to the unbalance of synthesis and degradation of the extracellular matrix of the joint cartilage. The final result is an accelerated destruction of the extracellular matrix, mainly by proteolytic enzymes of chondrocytes and of synovial cells, followed by alterations in the repair systems of cartilage.

The aim was to study the effect of hyaluronic acid (HA), of dermatan sulphate (DS) and of the compositions of the invention, made of a mixture of hyaluronic acid and dermatan sulphate (HA+DS), on the metalloprotease activity in human chondrocytes.

Two compositions were used consisting of a mixture of hyaluronic acid and dermatan sulphate in a weight ratio of 1:0.25.

Materials and Methods

Solutions were prepared with the two compositions of the invention. One of them contained 160 µg/ml of hyaluronic acid and 40 µg/ml of dermatan sulphate, and was compared to hyaluronic acid at a concentration of 160 µg/ml and to dermatan sulphate at a concentration of 40 µg/ml. The other composition contained 800 µg/ml of hyaluronic acid and 200 µg/ml of dermatan sulphate and was compared to hyaluronic acid at a concentration of 800 µg/ml and to dermatan sulphate at a concentration of 200 µg/ml.

The chondrocytes were isolated from cartilage pieces (from knee or hip) from pacientes with advanced osteoarthritis, by sequential enzymatic digestion: 1 hour with hyaluronidase (0.1 mg/ml), followed by 10 hours with collagenase (type IA, 2 mg/ml) at 37° C. in DMEM/Ham's F12 medium plus penicillin (100 U/ml) and streptomycin (100 µg/ml) in a controlled $CO_2$ atmosphere. The product of the digestion was filtered (70 µm), washed and centrifuged. Cell viability was determined by the Trypan blue exclusion method, which was in excess of 95%. The isolated chondrocytes were seeded at 2.5×10 5 cells/well in 6-well plaques and incubated in DMEM/Ham's F-12 medium with penicillin (100 U/ml) and streptomycin (100 µg/ml) supplemented with human serum (10%) in a humidified incubator with 5% CO2 and at 37° C. Cells were grown to confluence.

In order to determine the metalloprotease activity (MMP), chondrocytes were preincubated with the study product (compositions of the invention, hyaluronic acid or dermatan sulphate) or the reference inhibitor (llomastat) for 24 hours and then chondrocytes were stimulated with 100 U/ml of IL-1β (interleuquin-1β) for 24 hours. The supernatants were centrifuged and treated with APMA (p-aminophenylmercuric acetate) during 4-5 hours at 37° C. Subsequently, supernatants were transferred to a 96-well plaque for fluorescence analysis and the FRET substrate (QXLTM 520) was added for MMP-1-2-3-12-13. The plaque was shaked and fluorescence measured a different times with excitation and emission wavelengths set at 490 nm and 520 nm, respectively.

Assays were performed in quadruplicate (from the four different patients), with blank, control and study groups. The study group was made up of the study products (compositions of the invention, hyaluronic acid and dermatan sulphate) and a reference inhibitor. Each study product was assayed at two concentrations. Four assays were performed (a total of n=8 for each group). Means and standard errors were calculated, and an analysis of variance and Dunnett's t-test were performed. A difference was considered statistically significant when $p<0.05$.

Results

With 24 hours preincubation the compositions of the invention assayed (HA+DS), the hyaluronic acid (HA) and the dermatan sulphate (DS) caused the inhibition of the metalloprotease activity. The chondrocytes+IL-1β treated with both the 800 µg/l HA+200 µg/ml DS composition (FIG. 3) and the 160 µg/ml HA+40 µg/ml DS composition (FIG. 4) showed a statistically significant reduction of metalloprotease activity ($p<0.05$). The reduction was more marked with the 800 µg/ml HA+200 µg/ml DS composition (FIG. 3).

Chondrocytes+IL-1β treated with hyaluronic acid (HA) or with dermatan sulphate also showed a reduction of metalloprotease activity, albeit not at a statistically significant level.

Figure 3:
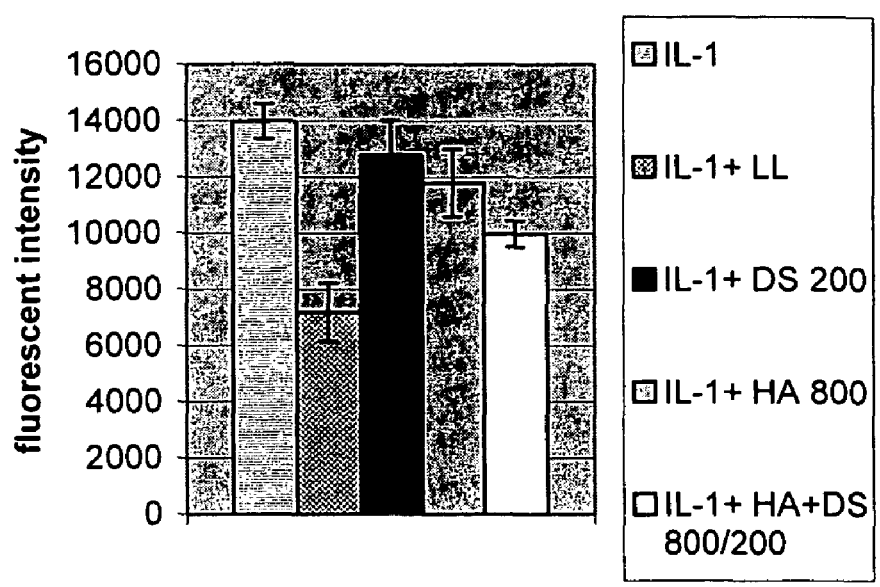
FIG. 3 represents the inhibition of the metalloprotease activity due to a composition of the invention (800 µg/ml HA+200 µg/ml DS), hyaluronic acid (HA, 800 µg/ml), dermatan sulphate (DS, 200 µg/ml) and llomastat (LL).
Figure 4:
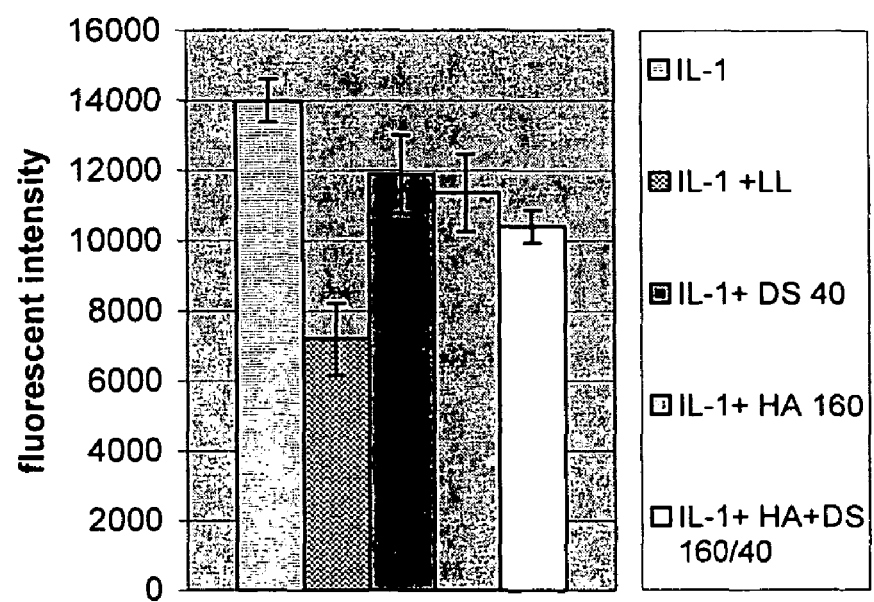
FIG. 4 represents the inhibition of the metalloprotease activity due to a composition according to the invention (160 µg/ml HA+40 µg/ml DS), hyaluronic acid (HA, 160 µg/ml), dermatan sulphate (DS, 40 µg/ml) and llomastat (LL).

As shown in FIGS. 3 and 4, significant differences were found between the two compositions of the invention assayed (hyaluronic acid+dermatan sulphate) and the hyaluronic acid.

Conclusions

The assayed compositions of the invention consisting of a mixture of hyaluronic acid and dermatan sulphate act synergically (see FIGS. 3 and 4).

In FIG. 3, the inhibitory activity of the 800 µg/ml HA+200 µg/ml DS composition is larger than the mere additive effect of the activity of the individual components.

Dermatan sulphate enhance the activity of the hyaluronic acid.

Based on the relation between the increased metalloprotease activity and osteoarthritis, it can be stated that dermatan sulphate enhances the antiarthrosic activity of the hyaluronic acid.

EXAMPLE 4

Clinical Trial in Adults with Osteoarthritis of the Knee

The objective of the randomized, double-blind, placebo-controlled clinical trial was to determine the comparative differences between a composition of the invention and placebo in overall pain relief and quality of life in a total sample of 20 patients with diagnosed osteoarthritis (OA) of the knee.

Another objective was to determine the safety and tolerability of a composition of the invention as determined by the adverse events, physical examination and vital signs.

Methods

Twenty patients (9 adult males and 11 adult females), aged 40 and over, with a clinical diagnosis of osteoarthritis of the knee(s) and verified knee pain for at least 15 days in the month prior to testing were enrolled in the study.

Patients received 80 mg of a composition of invention which contained 55% of hyaluronic acid, 15% of dermatan sulphate, 15% of collagen hydrolysate and 4% of nucleic acids (weight ratio: 1:0.27:0.27:0.07) or a placebo daily for 2 months.

The Western Ontario and McMaster Universities Osteoarthritis Index (WOMAC) and the SF-36v2 Quality of Life instrument scales were used in the study The WOMAC is a disease-specific, self-administered, health status measure. It probes clinically-important symptoms in the areas of pain, stiffness and physical function in patients with osteoarthritis of the hip and/or knee. The index consists of 24 questions (5-pain, 2-stiffness and 17-physical function) and can be completed in less than 5 minutes. The WOMAC is a valid, reliable and sensitive instrument for the detection of clinically important changes in health status following a variety of interventions (pharmacologic, nutritional, surgical, physiotherapy, etc.). The WOMAC questionnaire is valid for assessing the effects of intervention on hip or knee osteoarthritis.

The SF-36v2 Quality of Life instrument is a multi-purpose, short-form health survey with 36 questions. It yields an 8-scale profile of functional health and well-being scores as well as psychometrically-based physical and mental health summary measures and a preference-based health utility index. It is a generic measure, as opposed to one that targets a specific age, disease, or treatment group.

Accordingly, the SF-36v2 has proven useful in surveys of general and specific populations, comparing the relative burden of diseases, and in differentiating the health benefits produced by a wide range of different treatments. The SF-36v2 yields information on the following aspects and subsets of health; Physical Health (comprised of physical functioning, role-physical, bodily pain and general health) and Mental Health (comprised of vitality, social functioning, role-emotional and mental health).

Results:

Change in Bodily Pain

The improvement in SF-36v2 bodily pain was statistically significant in patients treated with the composition of the invention as compared with placebo ($p=0.031$).

A higher score is better because it means the patient feels less pain after taking the product.

Figure 5:
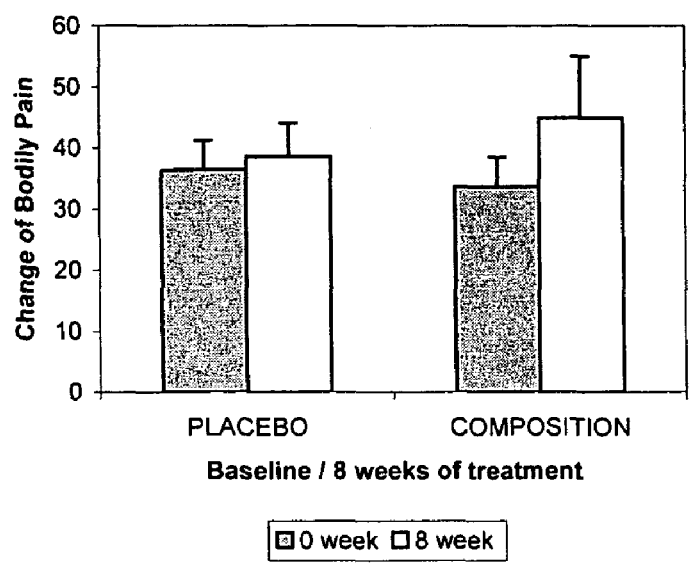
FIG. 5 shows the average change from baseline in the SF-36 bodily-pain score for both groups (composition of the invention and placebo) during the trial.

There was a 33% improvement in the bodily-pain score in the group that received the composition of invention versus a 6% improvement in the placebo group (see FIG. 5).

Change in Role-Physical Score

The superior effect of the composition of the invention compared with the placebo was statistically significant in week 4 in terms of role limitations due to physical health (role physical).

A higher score is better because it means that the patient noticed a physical improvement and a reduction in the limitations suffered in activities of daily living.

Figure 6:
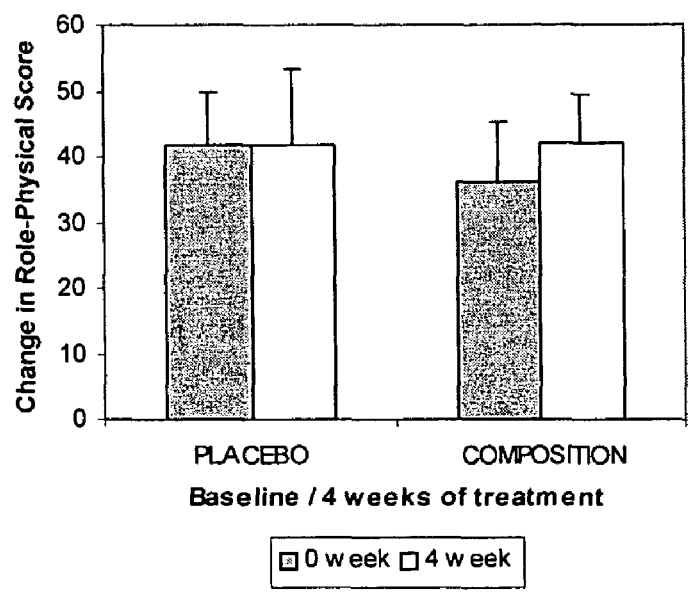
FIG. 6 shows the average change from baseline in the SF-36 role-physical score for both groups (composition of the invention and placebo) at week 4.

There was a 14% improvement in the role-physical score in the group that received the composition of invention versus an improvement of less than 1% in the placebo group (see FIG. 6).

Change in the Total WOMAC Score

Figure 7:
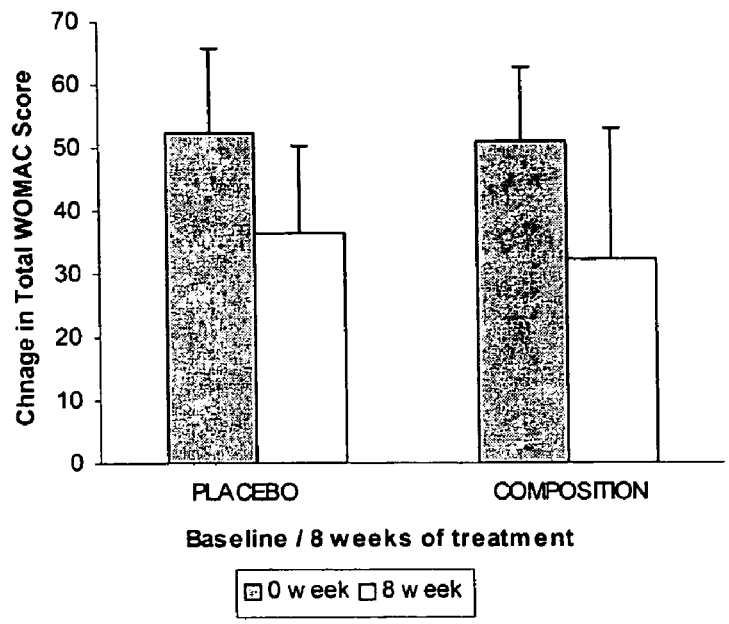
FIG. 7 shows the average change from baseline in the total WOMAC score for both groups (composition of the invention and placebo) during the trial.

There was a general trend in the course of the study for the total WOMAC score to improve significantly in the group treated with the composition of the invention compared with the placebo group (a lower score is better; see FIG. 7).

Change in WOMAC ADL

The improvement in activities of daily living (measured as a WOMAC ADL sub-score) was greater in the group treated with the composition of the invention than in the placebo group.

Figure 8:
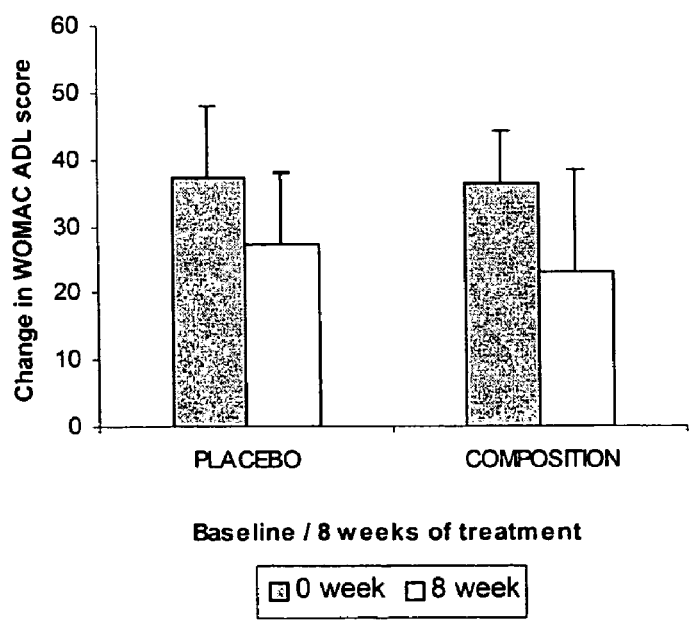
FIG. 8 shows the average change from baseline in the WOMAC ADL score for both groups (composition of the invention and placebo) during the trial.

There was a 36% improvement in the WOMAC ADL score in the group treated with the composition of the invention (a lower score is better; see FIG. 8).

Safety Analysis

No serious adverse events were reported during the study. A few mild adverse events were reported by 3 of the 20 patients enrolled, but they were considered to be unrelated to the study product.

CONCLUSIONS

It can be concluded that the trial shows the efficacy of the composition of the invention in improving the quality of life of patients with osteoarthritis of the knee.

The results of the trial also show the product's safety and tolerance, given that no serious adverse effects were found.

The efficacy of the compositions in the present invention can also be established through studies on horses in order to evaluate joint movement; and by using in vitro studies to determine the ability of compositions of the present invention to inhibit IL-1-induced agrecan degradation, conducting the assay on condrocyte cultures.

What is claimed is:

1. A method of treatment of osteoarthritis in a mammal comprising orally administering to a mammal in need thereof, a synergistic composition comprising hyaluronic acid and dermatan sulfate wherein the hyaluronic acid dermatan sulfate are present in a weight ratio of between 1:0.05 and 1:0.07.

2. The method of claim 1, wherein dermatan sulfate is present in the composition in an efficacious amount for enhancing anti-osteoarthritic activity of hyaluronic acid.

3. The method of claim 1, wherein hyaluronic acid and dermatan sulfate are present in said composition in a weight ratio of between 1:0.1 and 1:0.5.

4. The method of claim 1, wherein the composition further comprises collagen hydrolysate.

5. The method of claim 4, wherein hyaluronic acid, dermatan sulfate and collagen hydrolysate are present in said composition in a weight ratio of between 1:0.05:0.05 and 1:0.7:0.7.

6. The method of claim 5, wherein hyaluronic acid, dermatan sulfate and collagen hydrolysate are present in said composition in a weight ratio of between 1:0.1:0.1 and 1:0.5:0.5.

7. The method of claim 1, wherein the composition further comprises collagen hydrolysate and nucleic acids.

8. The method of claim 1, wherein said composition is in the form of a food or a food supplement for nourishing the joint.

9. The method of claim 8, wherein synovial fluid present in the joint is nourished.

10. The method of claim 1, wherein said composition is in the form of a food or a food supplement for improving articular mobility.

11. The method of claim 8, wherein the composition further comprises collagen hydrolysate.

12. The method of claim 11, wherein hyaluronic acid, dermatan sulfate and collagen hydrolysate are present in said composition in a weight ratio of between 1:0.1:0.1 and 1:0.5:0.5.

13. The method of claim 8, wherein the composition further comprises collagen hydrolysate and nucleic acids.

14. The method of claim 10, wherein the composition further comprises collagen hydrolysate.

15. The method of claim 14, wherein hyaluronic acid, dermatan sulfate and collagen hydrolysate are present in said composition in a weight ratio of between 1:0.1:0.1 and 1:0.5:0.5.

16. The method of claim 10, wherein the composition further comprises collagen hydrolysate and nucleic acids.

* * * * *

UNITED STATES PATENT AND TRADEMARK OFFICE
CERTIFICATE OF CORRECTION

PATENT NO. : 7,763,594 B2
APPLICATION NO. : 11/605453
DATED : July 27, 2010
INVENTOR(S) : Josep F. Escaich et al.

It is certified that error appears in the above-identified patent and that said Letters Patent is hereby corrected as shown below:

In claim 1 at column 12, line 2:
Insert --and-- between 'wherein the hyaluronic acid' and 'dermatan sulfate'

In claim 1 at column 12, line 3:
Remove "1:0.07" and insert --1:0.7--

In claim 2 at column 12, line 4:
Insert --the-- between 'wherein' and 'dermatan sulfate'

In claim 2 at column 12, line 6:
Insert --the-- between 'of' and 'hyaluronic acid'

In claim 3 at column 12, line 7:
Insert --the-- between 'wherein' and 'hyaluronic acid'

In claim 5 at column 12, line 12:
Insert --the-- between 'wherein' and 'hyaluronic acid,' and between 'hyaluronic acid,' and 'dermatan sulfate'

In claim 5 at column 12, line 13:
Insert --the-- between 'and' and 'collagen hydrolysate'

In claim 6 at column 12, line 16
Insert --the-- between 'wherein' and 'hyaluronic acid,' and between 'hyaluronic acid,' and 'dermatan sulfate'

In claim 6 at column 12, line 17:
Insert --the-- between 'and' and 'collagen hydrolysate'

In claim 12 at column 12, line 31:
Insert --the-- between 'wherein' and 'hyaluronic acid,'

Signed and Sealed this

Twenty-sixth Day of October, 2010

David J. Kappos
*Director of the United States Patent and Trademark Office*

In claim 12 at column 12, line 32:
Insert --the-- before 'dermatan sulfate' and between 'and' and 'collagen hydrolysate'

In claim 15 at column 12, line 39:
Insert --the-- between 'wherein' and 'hyaluronic acid,'

In claim 15 at column 12, line 40:
Insert --the-- before 'dermatan sulfate' and between 'and' and 'collagen hydrolysate'